(12) United States Patent
Pascual Gilabert et al.

(10) Patent No.: US 10,184,142 B2
(45) Date of Patent: Jan. 22, 2019

(54) BIOCATALYTIC PRODUCTION OF NUCLEOSIDE ANALOGUES AS ACTIVE PHARMACEUTICAL INGREDIENTS

(71) Applicant: PLASMIA BIOTECH, S.L., Barcelona (ES)

(72) Inventors: Marta Pascual Gilabert, Barcelona (ES); Victor Manuel Deroncelé Thomas, Barcelona (ES); Rafael Montilla Arévalo, Barcelona (ES)

(73) Assignee: Plasmia Biotech, S.L., Barcelona (ES)

( * ) Notice: Subject to any disclaimer, the term of this patent is extended or adjusted under 35 U.S.C. 154(b) by 0 days.

(21) Appl. No.: 14/787,678

(22) PCT Filed: Apr. 29, 2014

(86) PCT No.: PCT/EP2014/058761
§ 371 (c)(1),
(2) Date: Oct. 28, 2015

(87) PCT Pub. No.: WO2014/177585
PCT Pub. Date: Nov. 6, 2014

(65) Prior Publication Data
US 2016/0076070 A1    Mar. 17, 2016

Related U.S. Application Data

(60) Provisional application No. 61/817,064, filed on Apr. 29, 2013.

(51) Int. Cl.
*C12P 19/38* (2006.01)
*C12P 19/40* (2006.01)
*C12N 9/10* (2006.01)

(52) U.S. Cl.
CPC .......... *C12P 19/385* (2013.01); *C12N 9/1077* (2013.01); *C12P 19/40* (2013.01)

(58) Field of Classification Search
CPC ....... C12P 19/40; C12P 19/385; C12N 9/1077
USPC ................................................... 435/87, 88
See application file for complete search history.

(56) References Cited

U.S. PATENT DOCUMENTS 7,229,797 B1   6/2007 Tischer et al.
2008/0299608 A1* 12/2008 Kaminski ............ C12N 15/102
                                                           435/69.1

FOREIGN PATENT DOCUMENTS

WO        0114566 A2    3/2011
WO     2014072487 A1    5/2014

OTHER PUBLICATIONS

Devos et al., (Proteins: Structure, Function and Genetics, 2000, vol. 41: 98-107.*
Witkowski et al., (Biochemistry 38:11643-11650, 1999.*
Kisselev L., (Structure, 2002, vol. 10: 8-9.*
Whisstock et al., (Quarterly Reviews of Biophysics 2003, vol. 36 (3): 307-340.*
Database UniProt [Online]; Apr. 3, 2013; XP002732334.
Medici, R., et al.; Microbial synthesis of 2,6-diaminopurine nucleosides, Journal of Molecular Catalysis, 2006, pp. 40-44, vol. 39.
International Search Report, dated Nov. 28, 2014.

* cited by examiner

*Primary Examiner* — Robert B Mondesi
*Assistant Examiner* — Mohammad Y Meah
(74) *Attorney, Agent, or Firm* — Tristan A. Fuierer

(57) ABSTRACT

A biocatalytic process for producing active pharmaceutical ingredients (APIs) or intermediates thereof, wherein those APIs or their intermediates are nucleoside analogues (NAs) of formula I

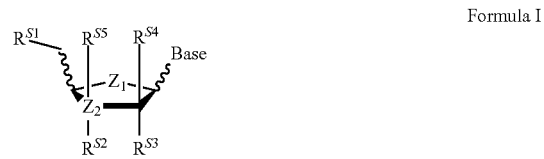

Formula I and wherein said NAs are active as pharmaceutically relevant antivirals and anticancer medicaments, intermediates or prodrugs thereof.

5 Claims, No Drawings

Specification includes a Sequence Listing.

```
                       SEQUENCE LISTING

<160> NUMBER OF SEQ ID NOS: 20

<210> SEQ ID NO 1
<211> LENGTH: 474
<212> TYPE: DNA
<213> ORGANISM: Lactobacillus delbrueckii

<400> SEQUENCE: 1
atgccaaaaa agacgatcta cttcggtgcc ggctggttca ctgaccgcca aaacaaagcc      60
tacaaggaag ccatggaagc cctcaaggaa aacccaacga ttgacctgga aaacagctac     120
gttcccctgg acaaccagta caagggtatc cgggttgatg aacacccgga atacctgcat     180
gacaaggttt gggctacggc cacctacaac aacgacttga acgggatcaa gaccaacgac     240
atcatgctgg gtgtctacat ccctgacgaa gaagacgtcg gcctgggcat ggaactgggt     300
tacgccttga gccaaggcaa gtacgtcctt ttggtcatcc cggacgaaga ctacggcaag     360
ccgatcaacc tcatgagctg gggcgtcagc gacaacgtga tcaagatgag ccagctgaag     420
gacttcaact tcaacaagcc gcgcttcgac ttctacgaag gtgccgtata ctaa           474

<210> SEQ ID NO 2
<211> LENGTH: 157
<212> TYPE: PRT
<213> ORGANISM: Lactobacillus delbrueckii

<400> SEQUENCE: 2

Met Pro Lys Lys Thr Ile Tyr Phe Gly Ala Gly Trp Phe Thr Asp Arg
1               5                   10                  15

Gln Asn Lys Ala Tyr Lys Glu Ala Met Glu Ala Leu Lys Glu Asn Pro
            20                  25                  30

Thr Ile Asp Leu Glu Asn Ser Tyr Val Pro Leu Asp Asn Gln Tyr Lys
        35                  40                  45

Gly Ile Arg Val Asp Glu His Pro Glu Tyr Leu His Lys Val Trp
    50                  55                  60

Ala Thr Ala Thr Tyr Asn Asn Asp Leu Asn Gly Ile Lys Thr Asn Asp
65                  70                  75                  80
```

Ile Met Leu Gly Val Tyr Ile Pro Asp Glu Asp Val Gly Leu Gly
            85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Asn Leu Met Ser Trp Gly
            115                 120                 125

Val Ser Asp Asn Val Ile Lys Met Ser Gln Leu Lys Asp Phe Asn Phe
130                 135                 140

Asn Lys Pro Arg Phe Asp Phe Tyr Glu Gly Ala Val Tyr
145                 150                 155

<210> SEQ ID NO 3
<211> LENGTH: 480
<212> TYPE: DNA
<213> ORGANISM: Lactobacillus lactis subsp. lactis

<400> SEQUENCE: 3
ttgaacaagt tgtttaatca agcagttaac gtttaccttg ccgcaccatt ttttagtgaa      60
agtcaaataa aaaagttgaa acttttagaa aatgcacttt caaaaaataa aacagtagca     120 aacttttta gcccaatgag atgtcaacat cctgaatctt taccacaaga agttgaagct     180 tttaccctg aatgggccaa agcgacaatg gaaaatgatg taaatgaggt aaataaagca     240
gatatcatcg ttgcaattgt tgatttcgat catcaagata ctgattctgg aacagcttgg     300
gagcttggct acgccatcgc tttagaaaaa ccaacctatc ttattcgttt tgaagatact     360
attccagcaa atataatgct cactgagcga aatagagctt tcttcaccca gattgaacaa     420
gttgaagaat atgatttttt agagtctaaa ctaatcccat atagtggaaa ataccagtag     480

<210> SEQ ID NO 4
<211> LENGTH: 159
<212> TYPE: PRT
<213> ORGANISM: Lactobacillus lactis subsp. lactis

<400> SEQUENCE: 4

Met Asn Lys Leu Phe Asn Gln Ala Val Asn Val Tyr Leu Ala Ala Pro
1               5                   10                  15

Phe Phe Ser Glu Ser Gln Ile Lys Lys Val Glu Leu Leu Glu Asn Ala
            20                  25                  30

Leu Ser Lys Asn Lys Thr Val Ala Asn Phe Phe Ser Pro Met Arg Cys
        35                  40                  45

Gln His Pro Glu Ser Leu Pro Gln Glu Val Glu Ala Phe Thr Pro Glu
    50                  55                  60

Trp Ala Lys Ala Thr Met Glu Asn Asp Val Asn Glu Val Asn Lys Ala
65                  70                  75                  80

Asp Ile Ile Val Ala Ile Val Asp Phe Asp His Gln Asp Thr Asp Ser
            85                  90                  95

Gly Thr Ala Trp Glu Leu Gly Tyr Ala Ile Ala Leu Glu Lys Pro Thr
            100                 105                 110

Tyr Leu Ile Arg Phe Glu Asp Thr Ile Pro Ala Asn Ile Met Leu Thr
            115                 120                 125

Glu Arg Asn Arg Ala Phe Phe Thr Gln Ile Glu Gln Val Glu Glu Tyr
            130                 135                 140

Asp Phe Leu Glu Ser Lys Leu Ile Pro Tyr Ser Gly Lys Tyr Gln
145                 150                 155

-continued

```
<210> SEQ ID NO 5
<211> LENGTH: 432
<212> TYPE: DNA
<213> ORGANISM: Thermofilum pendens Hrk 5

<400> SEQUENCE: 5
gtgaaggtct acctggcggc tccgatgagg ggtgaccgta gcgcgctggc aaacgtgaag      60
aagctgttgc aagccctgga ggagaggggg tacgtcgtgt tgacgaagca cgtagcggac     120
gacgtgctcg acgtggagaa gggtatgacg cctagagagg tcttcgagag ggatataagg     180
ttgctggaag aggcggacgt cctggtggcg gaggtatcgt acccgagcct cggcgtgggc     240
ttcgagatag cgtactttct gctgaggggg aagccggtga tagccctggc cttgcgcgag     300
aggctggaat cggtatccgc gatgataagg ggtataacgt gggagaactt caggctggta     360
gcctactcgg acgtcgacga ggcaatagaa aaattagaca gcatgttgcc aggtagcgtt     420
gacatgcaat ga                                                         432

<210> SEQ ID NO 6
<211> LENGTH: 143
<212> TYPE: PRT
<213> ORGANISM: Thermofilum pendens Hrk 5

<400> SEQUENCE: 6

Met Lys Val Tyr Leu Ala Ala Pro Met Arg Gly Asp Arg Ser Ala Leu
1               5                   10                  15

Ala Asn Val Lys Lys Leu Leu Gln Ala Leu Glu Glu Arg Gly Tyr Val
            20                  25                  30

Val Leu Thr Lys His Val Ala Asp Asp Val Leu Asp Val Glu Lys Gly
        35                  40                  45

Met Thr Pro Arg Glu Val Phe Glu Arg Asp Ile Arg Leu Leu Glu Glu
    50                  55                  60

Ala Asp Val Leu Val Ala Glu Val Ser Tyr Pro Ser Leu Gly Val Gly
65                  70                  75                  80

Phe Glu Ile Ala Tyr Phe Leu Leu Arg Gly Lys Pro Val Ile Ala Leu
                85                  90                  95

Ala Leu Arg Glu Arg Leu Glu Ser Val Ser Ala Met Ile Arg Gly Ile
            100                 105                 110

Thr Trp Glu Asn Phe Arg Leu Val Ala Tyr Ser Asp Val Asp Glu Ala
        115                 120                 125

Ile Glu Lys Leu Asp Ser Met Leu Pro Gly Ser Val Asp Met Gln
    130                 135                 140

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
catatgaagg tctacctggc g                                               21

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct
```

<400> SEQUENCE: 8
gaattcttgc atgtcaacgc tacc					24

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
caccatgaag gtctacctgg cgg					23

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
tcattgcatg tcaacgctac c						21

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
ttgcatgtca acgctacctg					20

<210> SEQ ID NO 12
<211> LENGTH: 22
<212> TYPE: DNA
<213> ORGANISM: Artificial Sequence
<220> FEATURE:
<223> OTHER INFORMATION: Synthetic Construct

<400> SEQUENCE: 12
ctcgagtcat tgcatgtcaa cg					22

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
ctcgagttgc atgtcaacgt ca					22

<210> SEQ ID NO 14
<211> LENGTH: 24
<212> TYPE: DNA
<213> ORGANISM: Artificial Sequence
<220> FEATURE:
<223> OTHER INFORMATION: Synthetic Construct

<400> SEQUENCE: 14
gaattctcat tgcatgtcaa cgtc					24

```
<210> SEQ ID NO 15
<211> LENGTH: 24
<212> TYPE: DNA
<213> ORGANISM: Artificial Sequence
<220> FEATURE:
<223> OTHER INFORMATION: Synthetic Construct

<400> SEQUENCE: 15
gaattcttgc atgtcaacgt cacc                                          24

<210> SEQ ID NO 16
<211> LENGTH: 28
<212> TYPE: DNA
<213> ORGANISM: Artificial Sequence
<220> FEATURE:
<223> OTHER INFORMATION: Synthetic Construct

<400> SEQUENCE: 16
ggaattccgc ttgcatgtca acgctacc                                      28

<210> SEQ ID NO 17
<211> LENGTH: 27
<212> TYPE: DNA
<213> ORGANISM: Artificial Sequence
<220> FEATURE:
<223> OTHER INFORMATION: Synthetic Construct

<400> SEQUENCE: 17
gccatatgaa caagttgttt aatcaag                                       27

<210> SEQ ID NO 18
<211> LENGTH: 28
<212> TYPE: DNA
<213> ORGANISM: Artificial Sequence
<220> FEATURE:
<223> OTHER INFORMATION: Synthetic Construct

<400> SEQUENCE: 18
gcgaattcta ctggtatttt ccactata                                      28

<210> SEQ ID NO 19
<211> LENGTH: 27
<212> TYPE: DNA
<213> ORGANISM: Artificial Sequence
<220> FEATURE:
<223> OTHER INFORMATION: Synthetic Construct

<400> SEQUENCE: 19
catatgccaa aaagacgat ctacttc                                        27

<210> SEQ ID NO 20
<211> LENGTH: 21
<212> TYPE: DNA
<213> ORGANISM: Artificial Sequence
<220> FEATURE:
<223> OTHER INFORMATION: Synthetic Construct

<400> SEQUENCE: 20
gtcgacttag tatacggcac c                                             21
```

BIOCATALYTIC PRODUCTION OF NUCLEOSIDE ANALOGUES AS ACTIVE PHARMACEUTICAL INGREDIENTS

CROSS-REFERENCE TO RELATED APPLICATIONS

This application is filed under the provisions of 35 U.S.C. § 371 and claims the priority of International Patent Application No. PCT/EP2014/058761 filed on 29 Apr. 2014 entitled "BIOCATALYTIC PRODUCTION OF NUCLEOSIDE ANALOGUES AS ACTIVE PHARMACEUTICAL INGREDIENTS" in the name of Marta PASCUAL GILABERT et al., which claims priority to U.S. Provisional Patent Application No. 61/817,064 filed on 29 Apr. 2013, both of which are hereby incorporated by reference herein in their entirety.

FIELD OF THE INVENTION

The present invention relates to novel enzymatic processes useful for the production of Nucleoside Analogues (NAs) active as pharmaceutically relevant antivirals and anticancer medicaments, intermediates or prodrugs thereof.

BACKGROUND OF THE INVENTION

Nucleoside analogues (NAs) are synthetic compounds structurally related to natural nucleoside. In terms of their structure, nucleosides are constituted by three key elements: (i) the hydroxymethyl group, (ii) the heterocyclic nitrogenous base moiety, and (iii) the furanose ring, which in several instances seems to act as a spacer presenting the hydroxymethyl group and the base in the correct orientation.

NAs are extensively used as antiviral and antitumor agents. These molecules have been traditionally synthesized by different chemical methods which often require time-consuming multistep processes including protection-deprotection reactions on the heterocyclic base and/or the pentose moiety to allow the modification of naturally occurring nucleosides (Boryski J. 2008. Reactions of transglycosylation in the nucleoside chemistry. Curr Org Chem 12:309-325). This time consuming multistep processes often lead to low yields and increased costs. Indeed, chemical methods usually increase the difficulty of obtaining products with correct stereo- and regioselectivity, generating secondary products (Condezo, L. A., et al. 2007. Enzymatic synthesis of modified nucleosides, p. 401-423. Biocatalysis in the pharmaceutical and biotechnology industries. CRC Press, Boca Raton, Fla., Mikhailopulo, I. A. 2007). Moreover, the chemical methods include the use of chemical reagents and organic solvents that are expensive and environmentally harmful.

Since several non-natural nucleosides acting as antiviral or anticancer agents have modifications on their sugar moiety, it is interesting to explore the possibility of developing a novel and effective industrial biocatalyst to catalyze the enzymatic synthesis of nucleosides analogues i.e. to develop a synthesis of active pharmaceutical ingredients (APIs) or their intermediates which can be applied on an industrial scale.

Surprisingly, it was found that the drawbacks of previous cited chemical synthesis routes can be avoided and NAs can be obtained with a conversion higher than 50% and/or an anomeric purity higher than 95%. That is possible based on the use of Nucleoside Desoxyribosyl Transferase (NDT or NdT) enzymes that we claim in the present invention.

The advantages of the NDT bioenzymatic synthesis are:
(i) One-pot synthesis,
(ii) Reduced number of steps,
(iii) Higher conversions and yields,
(iv) Avoidance of organic solvents in the enzymatic step,
(v) No protection/deprotection strategies, e.g. for the hydroxyl groups in the sugar, are needed,
(vi) Mild reaction conditions: environmentally-friendly technology (water or aqueous medium, neutral pH),
(vii) Extremely good selectivity: stereoselectivity—enantioselectivity, chemo-regioselectivity,
(viii) Fewer or no side reactions: impurity profile (reduced by-products content),
(ix) Reduction in overall waste generation,
(x) Process productivity,
(xi) Overall lower cost of production

DESCRIPTION OF THE INVENTION

The process described herein, using NDT enzymes is outlined as follows:

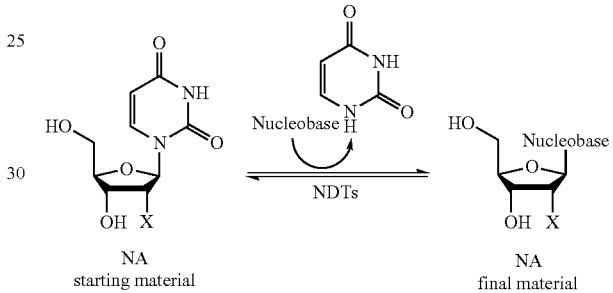

NA starting material     NA final material more precisely, as follows (where $Z_1$, $Z_2$, $R^{S1}$, $R^{S2}$, $R^{S3}$, $R^{S4}$, $R^{S5}$ are as defined herein):

Scheme 1. The catalyzed-reaction by NDTs

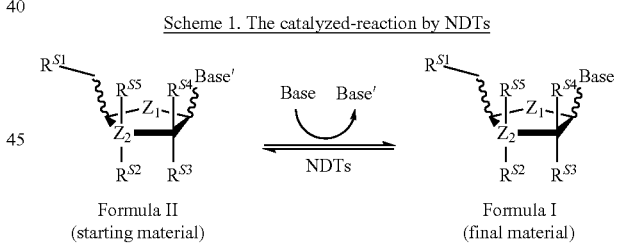

Formula II (starting material)     Formula I (final material)

For the purposes of present description, the following terms are further defined as follows.

The term "nucleoside" refers to all compounds in which a heterocyclic base is covalently coupled to a sugar, and especially preferred coupling of the nucleoside to the sugar includes a C1'-(glycosidic) bond of a carbon atom in a sugar to a carbon- or heteroatom (typically nitrogen) in the heterocyclic base. Therefore, in the present context the term "nucleoside" means the glycoside of a heterocyclic base.

As further used herein, the term "sugar" refers to all carbohydrates and derivatives thereof, wherein particularly contemplated derivatives include deletion, substitution or addition or a chemical group or atom in the sugar. For example, especially contemplated deletions include 2'-deoxy and/or 3'-deoxy sugars. Especially contemplated substitutions include replacement of the ring-oxygen with sulphur or methylene, or replacement of a hydroxyl group with a halogen, an amino-, sulthydryl-, or methyl group, and especially contemplated additions include methylene phosphonate groups. Further contemplated sugars also include sugar analogues (i.e., not naturally occurring sugars), and particularly carbocyclic ring systems. The term "carbocyclic ring system" as used herein refers to any molecule in which a plurality or carbon atoms form a ring, and in especially contemplated carbocyclic ring systems the ring is formed from 3, 4, 5, or 6 carbon atoms.

The term "nucleoside" may be used broadly as to include non-naturally occurring nucleosides, naturally occurring nucleosides as well as other nucleoside analogues. Illustrative examples of nucleosides are ribonucleosides comprising a ribose moiety as well as deoxyribonucleosides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

The term "nucleoside analogue", "NA" or "NAs" as used herein refers to all nucleosides, isomers or enantiomers thereof as well as racemates or enantio-enriched mixtures thereof, which are oxy- or deoxy-analogues of the naturally-occurring DNA and RNA nucleosides deoxycytidine, deoxyuridine, deoxyadenosine, deoxyguanosine and thymidine. Preferably, said NAs are nucleosides which comprise a sugar moiety and/or a base moiety which is different from the corresponding sugar moiety and/or base moiety of each of deoxycytidine, deoxyuridine, deoxyadenosine, deoxyguanosine or thymidine. More preferably, said NAs are non-naturally occurring nucleosides comprised of a sugar moiety and base moiety wherein at least one of said sugar moiety and said base moiety is not found in naturally-ocurring DNA or RNA, more preferably in naturally-occurring polynucleotides. Alternatively, said NAs are nucleosides in which the sugar is not a ribofuranose and/or in which the heterocyclic base is not a naturally occurring base (e.g., A, G, C, T, I, etc.). Similarly, the term "nucleotide" refers to a nucleoside, either D-nucleoside or L-nucleoside, to which a phosphate group is coupled to the sugar.

The term "one-step/one-pot", "one-step one-pot" or "one step-one pot" refers to a method of synthesis of chemical compounds through a single step in which the materials used are mixed together in a single vessel and allowed to react, rather than conducting the reaction in a sequence of separate stages. This strategy is used to improve reaction efficiency, increase yield and save time and resources.

The terms "heterocyclic ring" or "heterocyclic base" are used interchangeably herein and refer to any compound in which plurality of atoms form a ring via a plurality of covalent bonds, wherein the ring includes at least one atom other than a carbon atom. Particularly contemplated heterocyclic bases include 5- and 6-membered rings containing at least 1 to 4 heteroatoms each independently selected from nitrogen, oxygen and sulphur as the non-carbon atom (e.g., imidazole, pyrrole, triazole, dihydropyrimidine). Further contemplated heterocycles may be fused (i.e., covalently bound) to another ring or heterocycle, and are thus termed "fused heterocycle" or "fused heterocyclic base" as used herein. Especially contemplated fused heterocycles include a 5-membered ring fused to a 6-membered ring (e.g., purine, pyrrolo[2,3-d]pyrimidine), and a 6-membered ring fused to another 6-membered or higher ring (e.g., pyrido[4,5-d]pyrimidine, benzodiazepine). Examples of these and further preferred heterocyclic bases are given below. Still further contemplated heterocyclic bases may be aromatic, or may include one or more double or triple bonds. Moreover, contemplated heterocyclic bases and fused heterocycles may further be substituted in one or more positions. And any one of the rings being optionally substituted with one, two or three substituents each independently selected from the group consisting of halogen, hydroxy, nitro, cyano, carboxyl, C1-6alkyl, C1-6alkoxy, C1-6alkoxyC1-6alkyl, C1-6alkylcarbonyl, amino, mono- or diC1-6 alkyl amino, azido, mercapto, polyhaloC1-6alkyl, polyhaloC1-6alkoxy, and C3-7cycloalkyl.

The terms "nucleobase" covers naturally occurring nucleobases as well as non-naturally occurring nucleobases. It should be clear to the person skilled in the art that various nucleobases which previously have been considered "non-naturally occurring" have subsequently found in nature. Thus, "nucleobase" includes not only the known purine and pyrimidine heterocycles, but also heterocyclic analogues (such as N-substituted heterocycles) and tautomers thereof. See formulas A to H. Illustrative examples of nucleobases are adenine, guanine, thymine, cytosine, uracil, purine, xanthine, 2-chloroadenine, 2-fluoroadenine, pentyl(5-fluoro-2-oxo-1,2, dihydropyrimidin-4-yl)carbamate, cytosine N-alkyl carbamates, cytosine N-alkylesters, 5-azacytosine, 5-bromovinyluracil, 5-fluorouracil, 5-trifluromethyluracil, 6-methoxy-9H-purin-2-amine and (R)-3,6,7,8-tetrahydroimidazo[4,5-d][1,3]diazepin-8-ol.

The term "nucleobase" is intended to cover every and all of these examples as well as analogues and tautomers, and regioisomers thereof.

The term "tautomer" or "tautomeric form" refers to structural isomer of different energies which are interconvertible via a low energy barrier. For example, proton tautomers (also known as prototropic tautomers) include interconversion via migration of a proton, such as keto-enol and imine-enamine isomerizations. Valence tautomers include interconversions by reorganization of some of the bonding electrons.

The term "regioisomer" refers to structural isomer, or constitutional isomer in the sense that refers to molecules with the same molecular formula that whose atoms are bonded in different order of connectivity.

The term "conversion" refers to is the percentage of starting material that is transformed into products, either the expected final product, byproducts, or even into products of degradation.

The term "anomeric purity" refers to the amount of a particular anomer of a compound divided by the total amount of all anomers of that compound present in the mixture multiplied by 100%.

The term "2'-fluoro-arabino nucleoside-type" refers to any nucleoside analogue in which the carbon atom at the 2' position of the sugar moiety is substituted by a fluorine atom in a 2'-arabino configuration, independently of the nucleobase linked to the before mentioned sugar.

The term "intermediate" or "intermediates" refer to any nucleoside analogue type compounds which may be transformed into an active pharmaceutical ingredient (API) of nucleosidic structure by means of suitable additional chemical reactions. Therefore, intermediates are molecules that may be considered as API precursors. Any nucleoside analogue type compounds which are not used as APIs or their intermediates are disclaimed in the present invention.

Moreover, naturally-occurring DNA and RNA nucleosides and NAs which might have been disclosed in the prior art prepared by biocatalytic processes but which are unable to be produced on an industrial-scale at g/L using the method of the present invention (i.e. are only produced on a microlab demonstration scale or even at milligram quantities at lab scale not useful for production purposes) are disclaimed in the present invention since such NAs either cannot serve as APIs or be suitable for production on a commercial-scale, respectively.

Therefore summing up, by one hand, the chemical processes available in the prior art for industrial production of NAs are much more complex than the biocatalytic process of present invention. By the other hand, biocatalytic processes disclosed in the state of the art for the synthesis of nucleosides are limited to lab scale and to naturally occurring nucleosides, not to NAs, nor particularly at industrial scale, neither to APIs.

The terms "alkyl" and "unsubstituted alkyl" are used interchangeably herein and refer to any $C_1$-$C_{25}$ linear, branched, or cyclic hydrocarbon in which all carbon-carbon bonds are single bonds.

The terms "alkenyl" and "unsubstituted alkenyl" are used interchangeably herein and refer to any $C_1$-$C_{25}$ linear, branched, or cyclic alkyl with at least one carbon-carbon double bond.

Furthermore, the terms "alkynyl" and "unsubstituted alkynyl" are used interchangeably herein and refer to any $C_1$-$C_{25}$ linear, branched, or cyclic alkyl or alkenyl with at least one carbon-carbon triple bond. The terms "aryl" and "unsubstituted aryl" are used interchangeably herein and refer to any aromatic cyclic alkenyl or alkynyl, being as a group or part of a group is phenyl or naphthalenyl, each optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy. The term "alkaryl" is employed where an aryl is covalently bound to an alkyl, alkenyl, or alkynyl.

The term "substituted" as used herein refers to a replacement of an atom or chemical group (e.g., H, NH$_2$, or OH) with a functional group, and particularly contemplated functional groups include nucleophilic groups (e.g., —NH$_2$, —OH, —SH, —NC, etc.), electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —NH$_3^+$), and halogens (e.g., —F, —Cl), and all chemically reasonable combinations thereof. Thus, the term "functional group" and the term "substituent" are used interchangeably herein and refer to nucleophilic groups (e.g., —NH$_2$, —OH, —SH, —NC, —CN, etc.), electrophilic groups (e.g., C(O)OR, C(X)OH, C(Halogen)OR, etc.), polar groups (e.g., —OH), non-polar groups (e.g., aryl, alkyl, alkenyl, alkynyl, etc.), ionic groups (e.g., —NH$_3^+$), and halogens.

As also used herein, the terms "heterocycle" and "heterocyclic base" are used interchangeably herein and refer to any compound in which plurality of atoms form a ring via a plurality of covalent bonds, wherein the ring includes at least one atom other than a carbon atom. Particularly contemplated heterocyclic bases include 5- and 6-membered rings containing at least 1 to 4 heteroatoms each independently selected from nitrogen, oxygen and sulphur as the non-carbon atom (e.g., imidazole, pyrrole, triazole, dihydropyrimidine). Further contemplated heterocycles may be fused (i.e., covalently bound) to another ring or heterocycle, and are thus termed "fused heterocycle" or "fused heterocyclic base" as used herein. Especially contemplated fused heterocycles include a 5-membered ring fused to a 6-membered ring (e.g., purine, pyrrolo[2,3-d]pyrimidine), and a 6-membered ring fused to another 6-membered or higher ring (e.g., pyrido[4,5-d]pyrimidine, benzodiazepine). Examples of these and further preferred heterocyclic bases are given below. Still further contemplated heterocyclic bases may be aromatic, or may include one or more double or triple bonds. Moreover, contemplated heterocyclic bases and fused heterocycles may further be substituted in one or more positions. And any one of the rings being optionally substituted with one, two or three substituents each independently selected from the group consisting of halogen, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, and $C_{3-7}$cycloalkyl.

The nucleic acid molecule encoding an enzyme having N-deoxyribosyltransferase (NDT) activity according to present invention comprises:
a) a nucleotide sequence as shown in SEQ ID NO:1, SEQ. ID NO:3 or SEQ ID NO:5; or
b) a nucleotide sequence which is the complement of SEQ ID NO:1, SEQ. ID NO:3 or SEQ ID NO:5; or
c) a nucleotide sequence which is degenerate with SEQ ID NO:1, SEQ. ID NO:3 or SEQ ID NO:5; or
d) a nucleotide sequence hybridizing under conditions of high stringency to SEQ ID NO:1, SEQ. ID NO:3 or SEQ ID NO:5, to the complements of SEQ ID NO:1, SEQ. ID NO:3 or SEQ ID NO:5, or to a hybridization probe derived from SEQ ID NO:1, SEQ. ID NO:3 or SEQ ID NO:5, or their complement thereof; or
e) a nucleotide sequence having at least 80% sequence identity with SEQ ID NO:1, SEQ. ID NO:3 or SEQ ID NO:5; or
f) a nucleotide sequence having at least 65% sequence identity with SEQ ID NO:1, SEQ. ID NO:3 or SEQ ID NO:5, wherein said sequence preferably encodes or is complementary to a sequence encoding at least a NDT enzyme or a functional part thereof.
g) a nucleotide sequence encoding for an amino acid sequence selected from: SEQ ID NO:2, SEQ. ID NO:4 or SEQ ID NO:6.

Conditions of stringency hybridization in the sense of the present invention are defined as those described by Sambrook et al., Molecular Cloning, A Laboratory Manual, Cold Spring Harbor Laboratory Press (1989), 1.1011.104. According to this, hybridization under stringent conditions means that a positive hybridization signal is still observed after washing for one hour with 1×SSC buffer and 0.1% SDS at 55° C., preferably at 62° C. and most preferred at 68° C., in particular, for one hour in 0.2×SSC buffer and 0.1% SDS at 55° C., preferably at 62° C. and most preferred at 68° C.

Moreover, in the sense of present description, the invention also covers nucleotide or amino acid sequences which, on nucleotide or amino acidic levels, respectively, have an identity of at least 70%, particularly preferred at least 80% and most preferred at least 90% to the nucleotide or amino acid sequence shown in SEQ ID NO. 1, 3 or 5 (nucleotidic) or SEQ ID NO. 2, 4 or 6 (amino acidic). Percent identity is determined according to the following equation:

$$I=(n/L)\times 100$$

wherein I are percent identity, L is the length of the basic sequence and n is the number of nucleotide or amino acid difference of a sequence to the basic sequence.

Still another subject matter of the present invention is a recombinant vector comprising at least one copy of the nucleic acid molecule as defined above, operatively linked with an expression control sequence. The vector may be any prokaryotic or eukaryotic vector. Examples of prokaryotic vectors are chromosomal vectors such as bacteriophages (e.g. bacteriophage Lambda) and extrachromosomal vectors such as plasmids (see, for example, Sambrook et al., supra, Chapter 1-4). The vector may also be a eukaryotic vector, e.g. a yeast vector or a vector suitable for higher cells, e.g. a plasmid vector, viral vector or plant vector. Suitable eukaryotic vectors are described, for example, by Sambrook et al., supra, Chapter 16. The invention moreover relates to a recombinant cell transformed with the nucleic acid or the recombinant vector as described above. The cell may be any cell, e.g. a prokaryotic or eukaryotic cell. Prokaryotic cells, in particular, *E. coli* cells, are especially preferred.

For the purpose of present description, the invention also covers variants, or precursors, or orthologues, or combinations of SEQ ID Nos: 1-6.

The term "variant" as used throughout the specification is to be understood to mean a nucleotide sequence of a nucleic acid or amino acid sequence of a protein or polypeptide that is altered by one or more nucleotides or amino acids, respectively. The variant may have "conservative" changes, wherein a substituted nucleotide or amino acid has similar structural or chemical properties to the replaced nucleotide or amino acid. A variant may also have "non-conservative" changes or a deletion and/or insertion of one or more nucleotides or amino acids. The term also includes within its scope any insertions/deletions of nucleotides or amino acids for a particular nucleic acid or protein or polypeptide. A "functional variant" will be understood to mean a variant that retains the functional capacity of a reference nucleotide sequence or a protein or polypeptide.

The term "complement" or "complementary" as used herein may mean that each strand of 20 double-stranded nucleic acids such as, DNA and RNA, is complementary to the other in that the base pairs between them are non-covalently connected via two or three hydrogen bonds. For DNA, adenine (A) bases complement thymine (T) bases and vice versa; guanine (G) bases complement cytosine (C) bases and vice versa. With RNA, it is the same except that adenine (A) bases complement uracil (U) bases instead of thymine (T) bases. Since there is only one 25 complementary base for each of the bases found in DNA and in RNA, one can reconstruct a complementary strand for any single strand.

The term "orthologue" as used throughout the specification is to be understood as homologous gene or miRNAs sequences found in different species.

For the purposes of present description the term "NDT" means a biocatalyst pertaining to the family of the enzymes having nucleoside deoxyribosyltransferase or N-deoxyribosyl transferase activity. Said NDT may be a nucleoside deoxyribosyltransferase enzyme or N-deoxyribosyl transferase enzyme or may be another enzyme which has nucleoside deoxyribosyltransferase activity under specific reaction conditions and/or when said enzyme is modified to give nucleoside deoxyribosyltransferase activity, such as a glycosidase that is modified to catalyze the condensation reaction rather than the hydrolysis reaction (i.e. to carry out the glycosidase reaction in reverse), thereby behaving as a nucleoside deoxyribosyltransferase.

Also for the purposes of present description the term "Active Pharmaceutical Ingredient" or "API" means a compound, basically a NA, which shows therapeutic activity in human beings or animals. All the APIs disclosed in the present description are referred to under either any isomeric form, or as a racemic or enantiomerically-enriched mixture of isomers.

Present description discloses a biocatalytic process for producing active pharmaceutical ingredients (APIs) or intermediates thereof, being those APIs or their intermediates, nucleoside analogues (NAs), D isomers of formula I

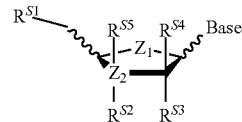

Formula I wherein,
$Z_1$ being O, $CH_2$, S, NH;
$Z_2$ being O, C, S, N, independently of $Z_1$;
$R^{S1}$ being hydrogen, methyl, OH, ether or ester thereof selected from:

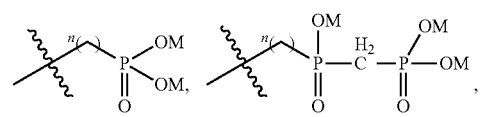

being n is 0 or 1 and M is hydrogen or a pharmaceutically acceptable counter-ion such as sodium, potassium, ammonium or alkylammonium;
$R^{S2}$ being hydrogen, halogen, preferably F, OH or an ether or ester residue thereof, CN, $NH_2$, SH, C≡CH, $N_3$;
$R^{S3}$ being hydrogen, in case of NA derived from deoxyribouclesides or being selected from: OH, $NH_2$, halogen (preferably F), $OCH_3$, when the NA is derived from ribonucleosides;
$R^{S4}$ being hydrogen, OH or an ether or ester residue thereof, $NH_2$, halogen, preferably F, providing $R^{S1}$ and $R^{S4}$ are different when both were ethers or esters of OH residues;
$R^{S5}$ being hydrogen, OH or an ether or ester residue thereof, $NH_2$ or halogen, preferably F;
Base bound to the ribose moiety being selected from those of formula A-H or their tautomers and regioisomers thereof:

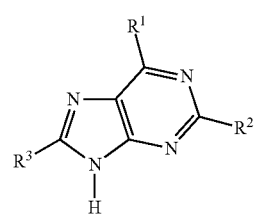

A

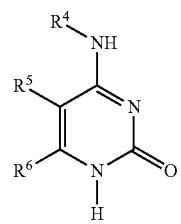

B

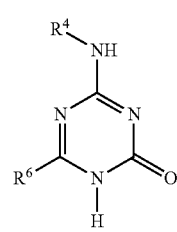

C

-continued

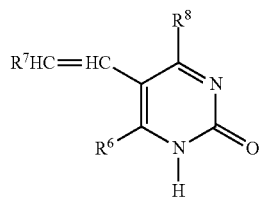

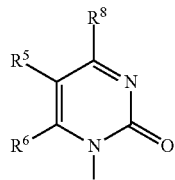

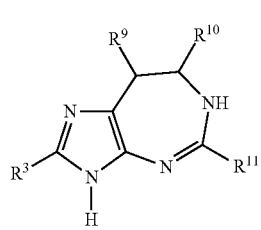

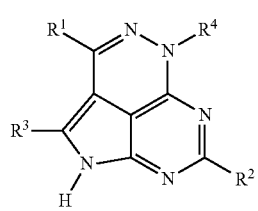

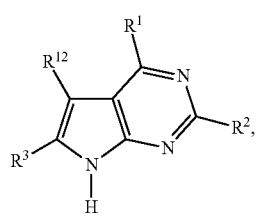

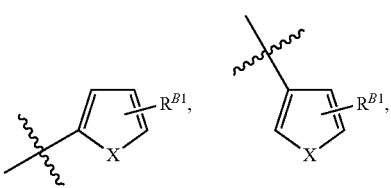 D

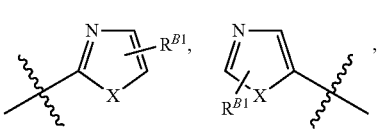 E

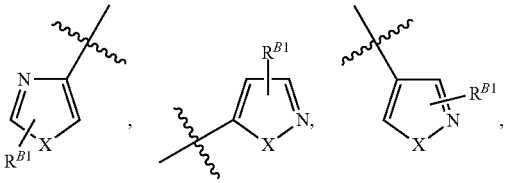 F

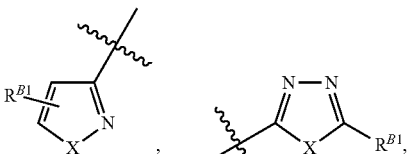 G

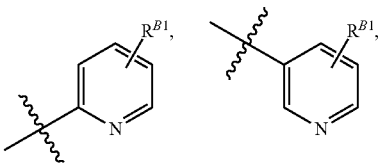 H

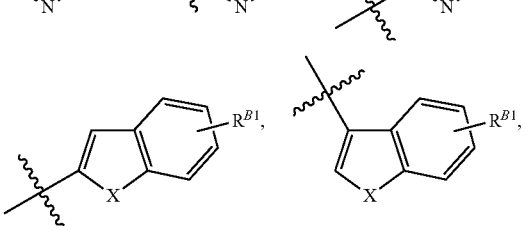

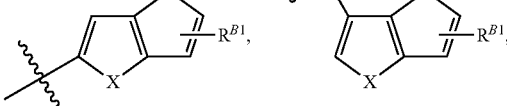

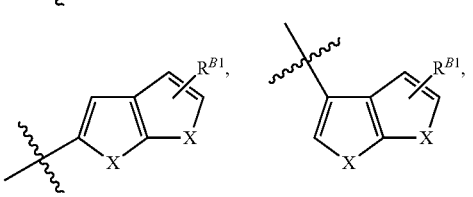

wherein, $R^1$ being hydrogen, methyl, optionally substituted alkyl chain, halogen, $OR^{13}$, $NR^{13}R^{14}$, $SR^{13}$;

$R^2$ being hydrogen, methyl, optionally substituted alkyl chain, halogen, $OR^{13}$, $NR^{13}R^{14}$, $SR^{13}$;

$R^3$ being hydrogen, methyl, optionally substituted alkyl chain;

$R^4$ being hydrogen, methyl, optionally substituted alkyl chain, $COR^{13}$, $CONR^{13}R^{14}$, $CO_2R^{13}$, $C(S)OR^{13}$, $CH_2$-heterocyclic ring;

$R^5$ being hydrogen, methyl, an optionally substituted alkyl chain, an optionally substituted alkenyl chain, an optionally substituted alkynyl chain, halogen, trihaloalkyl, $OR^{13}$, $NR^{13}R^{14}$, CN, $COR^{13}$, $CONR^{13}R^{14}$, $CO_2R^{13}$, $C(S)OR^{13}$, $OCONR^{13}R^{14}$, $OCO_2R^{13}$, $OC(S)OR^{13}$, $NHCONR^{13}R^{14}$, $NHCO_2R^{13}$, $NHC(S)OR^{13}$, $SO_2NR^{13}R^{14}$;

and any optionally substituted heterocycle or optionally substituted aryl of, independently, $R^1$, $R^2$, $R^3$, $R^4$ or $R^5$, selected from:

-continued

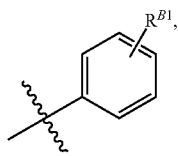

wherein

X being O, S, N—$R^{B2}$, Se; $R^{B1}$ being H, straight or branched $C_{1-10}$ alkyl, F, Cl, Br, I, X—$R^{B2}$, —C≡C—$R^{B2}$, $CO_2R^{B2}$; $R^{B2}$ being H, straight or branched $C_{1-5}$ alkyl, phenyl;

$R^6$ being hydrogen, optionally substituted alkyl chain;

$R^7$ being hydrogen, halogen, trihaloalkyl, $OR^{13}$, $NR^{13}R^{14}$, CN, $COR^{13}$, $CONR^{13}R^{14}$, $CO_2R^{13}$, $C(S)OR^{13}$;

$R^8$ being hydroxyl or amino, $OR^{13}$, $OSO_2R^{13}$, $NR^{13}R^{14}$, CN, $COR^{13}$, $CONR^{13}R^{14}$, $CO_2R^{13}$, $C(S)OR^{13}$;

$R^9$ being hydrogen, methyl, optionally substituted alkyl chain, halogen, $OR^{13}$, $NR^{13}R^{14}$, $COR^{13}$, $CONR^{13}R^{14}$, CN, $CO_2R^{13}$, $C(S)OR^{13}$, $OCONR^{13}R^{14}$, $OCO_2R^{13}$, $OC(S)OR^{13}$, $NHCONR^{13}R^{14}$, $NHCO_2R^{13}$, $NHC(S)OR^{13}$;

$R^{10}$ and $R^{11}$ are independently of each other hydrogen, methyl, optionally substituted alkyl chain;

$R^{12}$ being hydrogen, methyl, optionally substituted alkyl chain, halogen, $OR^{13}$, $NR^{13}R^{14}$, CN, $COR^{13}$, $CONR^{13}R^{14}$, $CO_2R^{13}$, $C(S)OR^{13}$, $OCONR^{13}R^{14}$, $OCO_2R^{13}$, $OC(S)OR^{13}$, $NHCONR^{13}R^{14}$, $NHCO_2R^{13}$, $NHC(S)OR^{13}$;

$R^{13}$ and $R^{14}$ are independently of each other hydrogen, substituted or unsubstituted alkyl chain, substituted or unsubstituted alkenyl chain, substituted or unsubstituted alkynyl chain, substituted or unsubstituted heterocyclic or phenyl rings;

the process being carried out in an one-step/one-pot reaction, wherein said reaction comprises the addition, in a suitable reaction aqueous medium and under suitable reaction conditions, of a nucleoside deoxyribosyltransferase enzyme (NDT) to a mixture of starting materials comprising at least a nucleoside, D isomer, of formula II

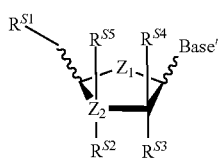

Formula II wherein, $Z_1$ being O, $CH_2$, S, NH;

$Z_2$ being O, C, S, N, independently of $Z_1$;

$R^{S1}$ being hydrogen, methyl, OH, ether or ester thereof selected from:

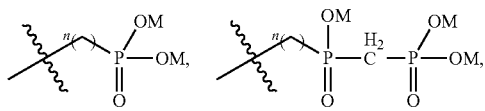

being n is 0 or 1 and M is hydrogen or a pharmaceutically acceptable counter-ion such as sodium, potassium, ammonium or alkylammonium;

$R^{S2}$ being hydrogen, halogen, preferably F, OH or an ether or ester residue thereof, CN, $NH_2$, SH, C≡CH, $N_3$;

$R^{S3}$ being hydrogen, in case of NA derived from desoxyribonucleosides or being selected from: OH, $NH_2$, halogen (preferably F), $OCH_3$, when the NA is derived from ribonucleosides;

$R^{S4}$ being hydrogen, OH or an ether or ester residue thereof, $NH_2$, halogen, preferably F, providing $R^{S1}$ and $R^{S4}$ are different when both were ethers or esters of OH residues;

$R^{S5}$ being hydrogen, OH or an ether or ester residue thereof, $NH_2$ or halogen, preferably F;

Base' bound to the ribose moiety, being selected from any group containing a heterocyclic ring;

and at least a free nucleobase, to be transferred by the NDT enzyme, being selected from:

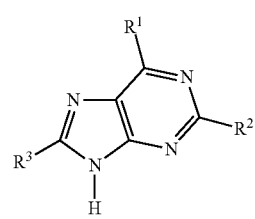

A'

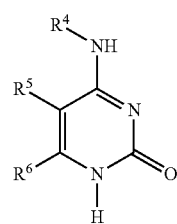

B'

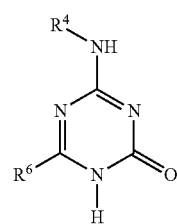

C'

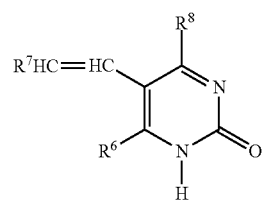

D'

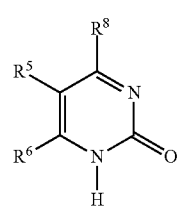

E'

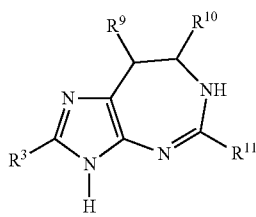

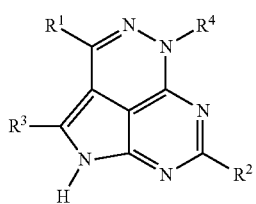

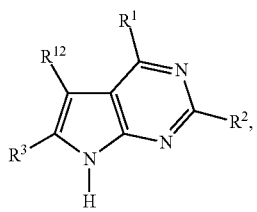

wherein,

R[1] being hydrogen, methyl, optionally substituted alkyl chain, halogen, $OR^{13}$, $NR^{13}R^{14}$, $SR^{13}$;

R[2] being hydrogen, methyl, optionally substituted alkyl chain, halogen, $OR^{13}$, $NR^{13}R^{14}$, $SR^{13}$;

R[3] being hydrogen, methyl, optionally substituted alkyl chain:

R[4] being hydrogen, methyl, optionally substituted alkyl chain, $COR^{13}$, $CONR^{13}R^{14}$, $CO_2R^{13}$, $(S)OR^{13}$, $CH_2$-heterocyclic ring;

R[5] being hydrogen, methyl, an optionally substituted alkyl chain, an optionally substituted alkenyl chain, an optionally substituted alkynyl chain, halogen, trihaloalkyl, $OR^{13}$, $NR^{13}R^{14}$, CN, $COR^{13}$, $CONR^{13}R^{14}$, $CO_2R^{13}$, $C(S)OR^{13}$, $OCONR^{13}R^{14}$, $OCO_2R^{13}$, $OC(S)OR^{13}$, $NHCONR^{13}R^{14}$, $NHCO_2R^{13}$, $NHC(S)OR^{13}$, $SO_2NR^{13}R^{14}$;

and any optionally substituted heterocycle or optionally substituted aryl of, independently, R[1], R[2], R[3], R[4] or R[5], selected from:

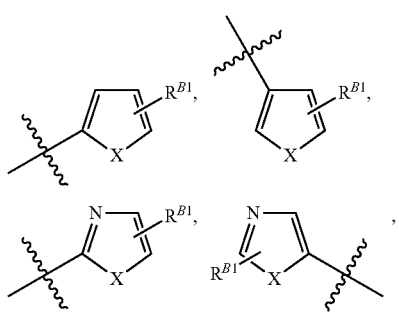

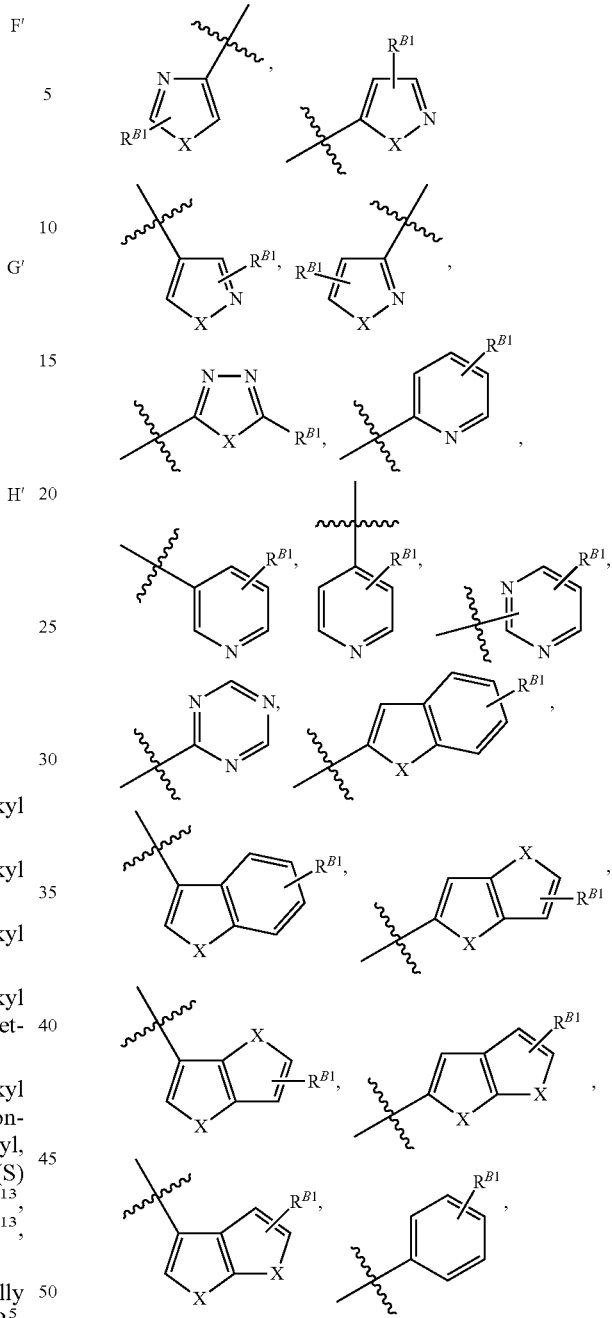

wherein

X being O, S, N—$R^{B2}$, Se; $R^{B1}$ being H, straight or branched $C_{1-10}$ alkyl, F, Cl, Br, I, X—$R^{B2}$, —C≡C—$R^{B2}$, $CO_2R^{B2}$; $R^{B2}$ being H, straight or branched $C_{1-5}$ alkyl, phenyl;

R[6] being hydrogen, optionally substituted alkyl chain;

R[7] being hydrogen, halogen, trihaloalkyl, $OR^{13}$, $NR^{13}R^{14}$, CN, $COR^{13}$, $CONR^{13}R^{14}$, $CO_2R^{13}$, $C(S)OR^{13}$, R[8] being hydroxyl or amino, $OR^{13}$, $OSO_2R^{13}$, $NR^{13}R^{14}$, CN, $COR^{13}$, $CONR^{13}R^{14}$, $CO_2R^{13}$, $C(S)OR^{13}$;

R[9] being hydrogen, methyl, optionally substituted alkyl chain, halogen, $OR^{13}$, $NR^{13}R^{14}$, $COR^{13}$, $CONR^{13}R^{14}$, CN, $CO_2R^{13}$, $C(S)OR^{13}$, $OCONR^{13}R^{14}$, $OCO_2R^{13}$, $OC(S)OR^{13}$, $NHCONR^{13}R^{14}$, $NHCO_2R^{13}$, $NHC(S)OR^{13}$;

$R^{10}$ and $R^{11}$ are independently of each other hydrogen, methyl, optionally substituted alkyl chain;

$R^{12}$ being hydrogen, methyl, optionally substituted alkyl chain, halogen, $OR^{13}$, $NR^{13}R^{14}$, CN, $COR^{13}$, $CONR^{13}R^{14}$, $CO_2R^{13}$, $C(S)OR^{13}$, $OCONR^{13}R^{14}$, $OCO_2R^{13}$, $OC(S)OR^{13}$, $NHCONR^{13}R^{14}$, $NHCO_2R^{13}$, $NHC(S)OR^{13}$;

$R^{13}$ and $R^{14}$ are independently of each other hydrogen, substituted or unsubstituted alkyl chain, substituted or unsubstituted alkenyl chain, substituted or unsubstituted alkynyl chain, substituted or unsubstituted heterocyclic or phenyl rings.

The heterocyclic ring constituting the base in formula II of the starting materials may be selected from: uracil, adenine, cytosine, guanine, thymine, hypoxanthine, xanthine, thiouracil, thioguanine, 9-H-purine-2-amine, 7-methylguanine, 5-fluorouracil, 5-bromouracil, 5-chlorouracil, 5,6-dihydrouracil, 5-methylcytosine and 5-hydroxymethylcytosine, pteridone, and any substituted derivative thereof. Preferably the heterocyclic ring constituting the base' in formula II of the starting materials is selected from: uracil, adenine, cytosine, guanine, thymine, hypoxanthine, xanthine, thiouracil, thioguanine, 9-H-purine-2-amine, 7-methylguanine, 5-fluorouracil, 5-bromouracil, 5-chlorouracil, 5,6-dihydrouracil, 5-methylcytosine and 5-hydroxymethylcytosine and any substituted derivatives thereof.

Moreover, the free nucleobase to be transferred by the NDT enzyme is, preferably, selected from:

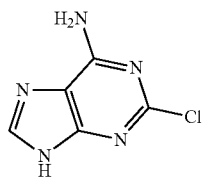

2-chloro-9H-purin-6-amine
(2-chloroadenine)

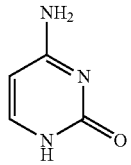

4-aminopyridmidin-2(1H)-one
(cytosine)

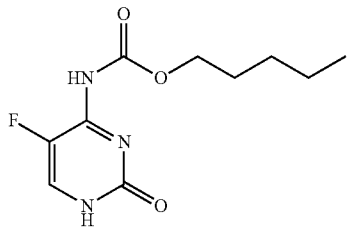

pentyl (5-fluoro-2-oxo-1,2-dihydropyrimidin-4-yl)carbamate

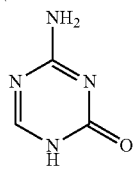

4-amino-1,3-5-triazin-2(1H)-one
(5-azacytosine)

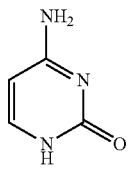

4-aminopyrimidin-2-(1H)-one
(cytosine)

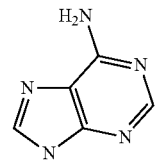

9H-purin-6-amine
(adenine)

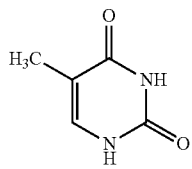

5-methylpyrimidine-2,4(1H,3H)-dione
(thymine; 5-methyluracil)

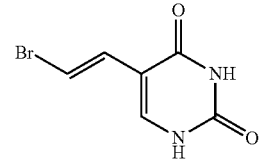

(E)-5-(2-bromovinyl)pyrimidine-
2,4(1H,3H)-dione
((E)-5-bromovinyluracil)

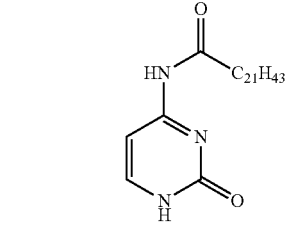

N-(2-oxo-1,2-dihyrdopyrimidin-4-yl)docosanamide

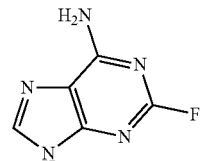

2-fluoro-9H-purin-6-amine
(2-fluoroadenine)

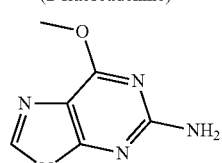

6-methoxy-9H-purin-2-amine

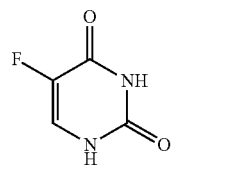

5-fluoropyrimidine-2,4(1H,3H)-dione
(5-fluorouracil)

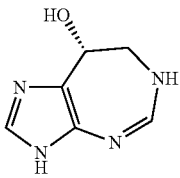

(R)-3,6,7,8-tetrahydroimidazo[4,5-d][1,3]diazepin-8-ol

In a preferred embodiment of the aforementioned process, $Z_2$ is C. With the process described herein, the APIs or intermediates thereof produced are selected from: Clofarabine (Cl-F-araA), Decitabine (aza-dCyd), Cytarabine (ara-C), Vidarabine, Brivudine, Enocitabine (BH-AC), Zalcitabine (ddC), Cladribine (Cl-dAdo), Fludarabine (F-araA), Nelerabine (MAY), Zidovudine, Floxuridine (FUDR), β-Thymidine, idoxuridine (IdU), trifluridine (TFT), acedurid (EdU), ribavirin, didanosine (ddI) and Pentostatin.

More preferably, the APIs or intermediates thereof produced are selected from: Clofarabine, Cytarabine, Vidarabine, Brivudine, Enocitabine, Zalcitabine, Cladribine, Fludarabine, Nelerabine, Zidovudine, Floxuridine and Pentostatin; yet more preferably the APIs or intermediates thereof produced are selected from Clofarabine, Cytarabine and Zidovudine (AZT); and still more preferably the described process is particularly intended to the industrial production of Clofarabine, Cytarabine and an intermediate of Zidovudine; furthermore preferably Clofarabine or intermediates thereof, yet even more preferably Clofarabine.

However, for the purpose of limiting the scope of present invention, the following NAs are specifically disclaimed: CAS No. 2627-62-5, CAS No. 7481-89-2, CAS No. 50-91-9, CAS No. 50-90-8, CAS No. 54-42-2, CAS No. 10356-76-0, CAS No. 2239-64-7, CAS No. 4546-70-7, CAS No. 15176-29-1, CAS No. 70-00-8, CAS No. 838-07-3, CAS No. 10212-20-1, but only with regard to a biocatalytic synthesis mediated by mesophilic NDT, wherein the pilot production of the aforementioned list of NAs did not render sufficient yields to scale-up that production to industry efficiently.

For the purposes of present description organisms from which the enzymes having NDT activity originate used may be mesophiles, thermophiles or hypermesophiles. Mesophiles or mesophilic are those able to work or to carry out a nucleoside deoxyribosyltransferase activity, at temperatures ranging from 18 to up 60° C., with an optimal temperature range of 40-55° C. Organisms or NDT enzymes, thermophiles or thermophilic are those able to work or to carry out a nucleoside deoxyribosyltransferase activity, at temperatures ranging over 60° C. and up to 80° C. Organisms or NDT enzymes, hyperthermophiles or hyperthermophilic, are those able to work or to carry out a nucleoside deoxyribosyltransferase activity, at temperatures over 80° C. and up to 100° C., with an optimal temperature range of 80-95° C.

Still in one more preferred embodiment of practicing the process describe hereto, the API, or intermediates thereof, produced is Clofarabine (Scheme 2).

Scheme 2. Synthesis of Clorafabine by using enzymes with nucleoside deoxyribosyltransferase (NDT) activity

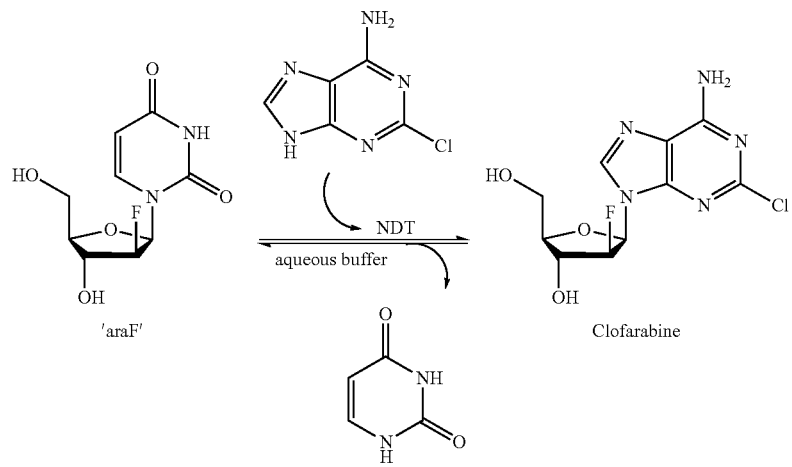

The process of invention applied to the production of clofarabine has several advantages over the industrial process used in the prior art for the chemical synthesis of this NA, the so called ILEX procedure (Bauta et al, Org. Proc. Res. Dev. 2004, 8, 889-896):
(i) One-pot synthesis,
(ii) Reduced number of steps,
(iii) Higher conversions and yields,
(iv) Avoidance of organic solvents in the enzymatic step,
(v) No protection/deprotection strategies are needed, e.g. for the hydroxyl groups in the sugar,
(vi) Mild reaction conditions: environmentally-friendly technology (water or aqueous medium, neutral pH),
(vii) Extremely good selectivity: stereoselectivity—enantioselectivity, chemo-regioselectivity,
(viii) Fewer or no side reactions: impurity profile (reduced by-products content), (ix) Reduction in overall waste generation,
(x) Process productivity
(xi) Overall lower cost of production Moreover, there are other additional advantages of the biocatalytic process of invention over the chemical process used in the prior art. Particularly relevant is the absence in the process of the invention of the organic solvents used in the chemical process of Bauta et al., as dichloromethane (DCM), acetonitrile (ACN), 1,2-dichloroethane (DCE), methanol, heptane, etc. . . . . . All those organic solvents must be removed prior to any process waste discharge to the environment. An supplementary inconvenient of ILEX process with regard to the procedure of invention is its complexity, as far as ILEX process comprises at least 3 procedure steps, against the single step-one pot process of invention.

The source of native or recombinant enzyme used in the process of the invention are Bacteria or Archaea organisms. Enzymes having nucleoside deoxyribosyltransferase activity used in the process of invention can be isolated from a microorganism selected from, as a way of example, Bacteria, particularly from *Lactobacillus* or *Lactococcus* species or from Archaea particularly from any of the following genus: *Thermofilum; Haloarcula; Natronococcus; Natrialba; Halobiforma; Methanosarcina; Methanomethylovorans; Methanoculleus; Methanosphaerula; Methanohalobium; Methanosalsum* or *Methanosaeta*.

Still another embodiment of present invention relates to the use in the process disclosed of a recombinant NDT enzyme comprising an amino acid sequence encoded by a nucleic acid sequence, or fragments thereof, isolated from Archaea.

As described all along present description one of the preferred embodiments for practicing the process of invention is based on the use as biocatalyst of NDT enzymes for performing the base transfer one step-one pot reaction. Preferably NDT enzymes are of recombinant type, comprising gene sequences of fragments thereof, encoding for NDT enzymatic activities able to carry out nucleobase transfer one step-one pot reactions, at temperatures ranging over 60° C. and up to 100° C. and, more preferably, at the suitable reaction conditions described herein.

Suitable conditions for carrying out the different embodiments of the process of invention comprise:
a) Temperature ranging 18-100° C., preferably 20-100° C., and more preferably ranging 40-100° C., furthermore preferably 50-100° C.
b) Reaction time ranging 1-600 h
c) Concentration of starting material ranging 1-500 mM
d) Stoichiometry nucleoside starting material:nucleobase ranges from 1:5 to 5:1.
e) Amount of enzyme having NDT activity or NDT enzyme ranging 0.001-100 mg/ml, preferably 0.001-10 mg/mL.
f) Free nucleobase added to the reaction medium, optionally dissolved in an organic solvent
g) Aqueous reaction medium optionally also containing up to 40% of a suitable organic solvent. Preferably up to 20% and more preferably up to 5%.

Preferred organic solvents to be added to the reaction medium or to be used for dissolving previously the free nucleobases are polar aprotic solvents, preferably selected from: Tetrahydrofuran, acetonitrile, acetone or Dimethylformamide (DMF).

The process according to present invention also includes an isolation and/or purification steps of the NA produced by standard operation means selected from: chromatography, precipitation, filtration, concentration or crystallization.

For the purposes also of present description, the term recombinant enzyme or recombinant type enzyme should be understood as a protein or enzyme that is derived from recombinant DNA. The term "recombinant DNA" is a form of DNA that does not exist naturally, which is created by combining DNA sequences that would not normally occur together.

The process of the invention, specifically covers the one wherein the API produced is Clofarabine (Scheme 2), the 2'-deoxyribonucleoside used as starting material is 2'-fluoro-arabinofuranosyl-2'-deoxyuridine, the nucleobase also used as starting material to be transferred by the NDT enzyme, is 2-chloroadenine and the NDT is a natural occurring NDT enzyme, isolated from *Lactobacillus delbrueckii* (formerly called *Lactobacillus leichmannii*).

One of the embodiments of the process of invention covers the one wherein the API produced is, Clofarabine (Scheme 2), the 2'-deoxyarabinonucleoside used as starting material, is any suitable 2'-fluoro-arabino-type, preferably 2'-fluoro-arabinofuranosyl-2'-deoxyuridine, the nucleobase also used as starting material to be transferred by the NDT enzyme, is 2-chloroadenine.

In another embodiment of the process of invention, the API produced is Cytarabine, the 2'-deoxyarabinonucleoside used as starting material, is arabinofuranosyl-2'-deoxyuridine, the nucleobase also used as starting material to be transferred by the NDT enzyme is cytosine.

In another embodiment of the process of invention, the API produced is an intermediate in the synthesis of Zidovudine, the nucleoside used as starting material is 3'-amino-2',3'-dideoxyadenosine, the nucleobase also used as starting material to be transferred by the NDT enzyme is thymine. Said intermediate of Zidovudine, thus obtained, comprises a primary amine moiety which may be readily transformed into zidovudine using a further azidation step using, for example inorganic azides or azo-transfer compounds such as trifluoromethanesulfonyl azide or imidazole-1-sulfonyl azide.

Forming part of the same inventive concept, present description also discloses recombinant nucleoside deoxyribosyltransferase enzymes (NDTs), able to carry out the process of the invention described above. The said native or recombinant NDT enzymes can be isolated from, bacteria preferably selected from *Lactobacillus delbrueckii* (formerly *Lactobacillus leichmannii*) or *Lactococcus lactis*; or from Archaea, preferably selected from: *Thermofilum pendens; Haloarcula sinaiiensis; Natronococcus amylolyticus; Natrialba hulunbeirensis; Halobiforma nitratireducens; Methanosarcina mazei; Methanomethylovorans hollandica; Methanoculleus bourgensis; Methanosphaerula palustres; Methanohalobium evestigatum; Methanosalsum zhilinae* or *Methanosaeta harundinacea*.

In one preferred embodiment of the invention, the NDT enzyme is obtained from
a) *Lactobacillus delbrueckii* (formerly called *Lactobacillus leichmannii*) nucleotide encoding sequence shown in SEQ ID NO 1; or
b) a nucleotide sequence which is the complement of SEQ ID. NO: 1; or
c) a nucleotide sequence which is degenerate with SEQ ID. NO: 1; or
d) a nucleotide sequence hybridizing under conditions of high stringency to SEQ ID. NO: 1, to the complement of SEQ ID. NO: 1, or to a hybridization probe derived from SEQ ID. NO: 1, or their complement thereof; or e) a nucleotide sequence having at least 80% sequence identity with SEQ ID. NO: 1; or
f) a nucleotide sequence having at least 65% sequence identity with SEQ ID. NO: 1, wherein said sequence preferably encodes or is complementary to a sequence encoding at least a NDT enzyme or a functional part thereof.
g) a nucleotide sequence encoding for a polypeptide having NDT activity, the amino acid sequence of which is at least 80% identical to the amino acid sequence shown in SEQ ID. NO: 2, further preferably a nucleotide sequence encoding for the amino acid sequence shown in SEQ ID. NO: 2.

In another preferred embodiment of the invention, the NDT enzyme is obtained from
a) *Lactococcus lactis* nucleotide encoding sequence shown in SEQ ID NO. 3 or
b) a nucleotide sequence which is the complement of SEQ ID. NO:3; or
c) a nucleotide sequence which is degenerate with SEQ ID. NO:3; or
d) a nucleotide sequence hybridizing under conditions of high stringency to SEQ ID. NO:3, to the complement of SEQ ID. NO:3, or to a hybridization probe derived from SEQ ID. NO:3, or their complement thereof; or
e) a nucleotide sequence having at least 80% sequence identity with SEQ ID. NO:3; or
f) a nucleotide sequence having at least 65% sequence identity with SEQ ID. NO:3, wherein said sequence preferably encodes or is complementary to a sequence encoding at least a NDT enzyme or a functional part thereof.
g) a nucleotide sequence encoding for a polypeptide having NDT activity, the amino acid sequence of which is at least 80% identical to the amino acid sequence shown in SEQ ID. NO:4, further preferably a nucleotide sequence encoding for the amino acid sequence shown in SEQ ID. NO:4.

In still other preferred embodiment of present invention the NDT enzyme is obtained from *Thermofilum pendens* nucleotide encoding sequence shown in SEQ ID NO. 5 or
a) a nucleotide sequence which is the complement of SEQ ID. NO:5; or
b) a nucleotide sequence which is degenerate with SEQ ID. NO:5; or
c) a nucleotide sequence hybridizing under conditions of high stringency to SEQ ID. NO:5, to the complement of SEQ ID. NO:5, or to a hybridization probe derived from SEQ ID. NO:5, or their complement thereof; or
d) a nucleotide sequence having at least 80% sequence identity with SEQ ID. NO:5; or
e) a nucleotide sequence having at least 65% sequence identity with SEQ ID. NO:5, wherein said sequence preferably encodes or is complementary to a sequence encoding at least a NDT enzyme or a functional part thereof.
f) a nucleotide sequence encoding for a polypeptide having NDT activity, the amino acid sequence of which is at least 80% identical to the amino acid sequence shown in SEQ ID. NO:6, further preferably a nucleotide sequence encoding for the amino acid sequence shown in SEQ ID. NO:6.

Also in the same line of integrating a single inventive linked concept, present description also discloses the use of a nucleoside deoxyribosyltransferase (NDT) in the production of APIs or intermediates thereof, being those APIs or their intermediates, nucleoside analogues (NAs) useful as anti-cancer or anti-viral medicaments. More preferably, the previously mentioned use is achieved by the production process and variants thereof, also previously detailed, of NAs as APIs or intermediates thereof. Particularly, related to that previously mentioned use, recombinant nucleoside deoxyribosyltransferases (NDTs) are preferred, in the production of APIs, being those APIs or their intermediates, nucleoside analogues (NAs) particularly useful as anti-cancer or anti-viral medicaments.

Among the APIs or intermediates thereof produced by such uses the following may be found: Clofarabine (Cl-F-araA), Decitabine (aza-dCyd), Cytarabine (ara-C), Vidarabine, Brivudine, Enocitabine (BH-AC), Zalcitabine (ddC), Cladribine (Cl-dAdo), Fludarabine (F-araA), Nelarabine (MAY), Zidovudine, Floxuridine (FUDR), β-Thymidine, idoxuridine (IdU), trifluridine (TFT), acedurid (EdU), ribavirin, didanosine (ddI) and Pentostatin.

More preferably, the APIs or intermediates thereof produced by the use of the enzymes disclosed herein, are selected from: Clofarabine, Cytarabine, Vidarabine, Brivudine, Enocitabine, Zalcitabine, Cladribine, Fludarabine, Nelarabine, Zidovudine, Floxuridine and Pentostatin; yet more preferably the APIs or intermediates thereof produced are selected from Clofarabine, Cytarabine and Zidovudine or intermediates thereof; and still more preferably the described uses are particularly dedicated to the industrial production of Clofarabine, Cytarabine and an intermediate of Zidovudine; furthermore preferably Clofarabine or intermediates thereof, yet more preferably Clofarabine.

Enzymes having N-deoxyribosyl transferase (NDT) activity to be used according to present invention include recombinant NDT enzymes encoded by a nucleic acid sequence selected from: SEQ ID No. 1, SEQ ID No. 3 or SEQ ID No. 5; or
a) a nucleotide sequence which is the complement of SEQ ID NO:1, SEQ. ID NO:3 or SEQ ID. NO:5; or
b) a nucleotide sequence which is degenerate with SEQ ID NO:1, SEQ. ID NO:3 or SEQ ID. NO:5; or
c) a nucleotide sequence hybridizing under conditions of high stringency to SEQ ID NO: 1, SEQ. ID NO:3 or SEQ ID. NO:5, to the complements of SEQ ID NO:1, SEQ. ID NO:3 or SEQ ID. NO:5, or to a hybridization probe derived from SEQ ID NO:1, SEQ. ID NO:3 or SEQ ID. NO:5, or their complement thereof; or
d) a nucleotide sequence having at least 80% sequence identity with SEQ ID NO:1, SEQ. ID NO:3 or SEQ ID. NO:5; or
e) a nucleotide sequence having at least 65% sequence identity with SEQ ID NO:1, SEQ. ID NO:3 or SEQ ID. NO:5, wherein said sequence preferably encodes or is complementary to a sequence encoding at least a NDT enzyme or a functional part thereof.
f) a nucleotide sequence encoding for an amino acid sequence selected from: SEQ ID NO:2, SEQ. ID NO:4 or SEQ ID NO:6.

Also included in present invention are recombinant expression vectors comprising sequences encoding a nucleoside deoxyribosyltransferase (NDT) operably linked to one or more control sequences that direct the expression or overexpression of said deoxyribosyltransferase in a suitable host. A preferred recombinant expression vector according to present invention is any carrying and expressing or overexpressing genes encoding said NDT enzymatic activities.

Preferred recombinant expression vectors according to present invention are carrying and expressing or overexpressing nucleic acid sequence selected from: SEQ ID No. 1, SEQ ID No. 3 or SEQ ID No. 5; or
  a) a nucleotide sequence which is the complement of SEQ ID NO:1, SEQ. ID NO:3 or SEQ ID NO:5; or
  b) a nucleotide sequence which is degenerate with SEQ ID NO:1, SEQ. ID NO:3 or SEQ ID NO:5 or; or
  c) a nucleotide sequence hybridizing under conditions of high stringency to SEQ ID NO: 1, SEQ. ID NO:3 or SEQ ID NO:5, to the complements of SEQ ID NO:1, SEQ. ID NO:3 or SEQ ID NO:5 or to a hybridization probe derived from SEQ ID NO:1, SEQ. ID NO:3 or SEQ ID NO:5, or their complement thereof; or
  d) a nucleotide sequence having at least 80% sequence identity with SEQ ID NO: 1, SEQ. ID NO:3, or SEQ ID NO:5; or
  e) a nucleotide sequence having at least 65% sequence identity with SEQ ID NO:1, SEQ. ID NO:3 or SEQ ID NO:5, wherein said sequence preferably encodes or is complementary to a sequence encoding at least a NDT enzyme or a functional part thereof.
    a nucleotide sequence encoding for an amino acid sequence selected from: SEQ ID NO:2, SEQ. ID NO:4 or SEQ ID NO:6.

The invention also covers the use of the recombinant expression vectors previously said, for the production either of recombinant NDT enzymes or for the production of active pharmaceutical ingredients (APIs) or intermediates thereof, being those APIs or their intermediates, nucleoside analogues (NAs) particularly useful as anti-cancer or anti-viral medicaments. Particularly APIs or intermediates thereof produced by the aforesaid use are selected from: Clofarabine (Cl-F-araA), Decitabine (aza-dCyd), Cytarabine (ara-C), Vidarabine, Brivudine, Enocitabine (BH-AC), Zalcitabine (ddC), Cladribine (Cl-dAdo), Fludarabine (F-araA), Nelerabine (MAY), Zidovudine, Floxuridine (FUDR), β-Thymidine, idoxuridine (IdU), trifluridine (TFT), acedurid (EdU), ribavirin, didanosine (ddl) and Pentostatin.

More preferably, the APIs or intermediates thereof produced are selected from: Clofarabine, Cytarabine, Vidarabine, Brivudine, Enocitabine, Zalcitabine, Cladribine, Fludarabine, Nelerabine, Zidovudine, Floxuridine and Pentostatin; yet more preferably the APIs or intermediates thereof produced are selected from Clofarabine, Cytarabine and Zidovudine; and still more preferably the expression vectors described herein are particularly suitable for industrial production of Clofarabine, Cytarabine and an intermediate of Zidovudine; furthermore preferably Clofarabine or intermediates thereof, yet even more preferably Clofarabine.

More preferably, the previously mentioned use for the production of APIs or intermediates thereof is achieved by the production process and variants thereof, also previously detailed.

The invention also covers host cells comprising the recombinant expression vectors, previously described, particularly when said host cell is *Escherichia coli*. Included as part of the same inventive single linked concept, the use of host cells comprising the recombinant expression vectors as previously described, for the production of recombinant NDTs, is also contemplated. Analogously, the use of host cells comprising the recombinant expression vectors as previously described, for the production of active pharmaceutical ingredients (APIs) or intermediates thereof, being those APIs or their intermediates, nucleoside analogues (NAs) useful as anti-cancer or anti-viral medicaments, is also part of present invention. Particularly if those host cells comprising the recombinant expression vectors as previously described, are used for producing APIs or intermediates thereof selected from: Clofarabine (Cl-F-araA), Decitabine (aza-dCyd), Cytarabine (ara-C), Vidarabine (araA), Brivudine, Enocitabine (BH-AC), Zalcitabine (ddC), Cladribine (Cl-dAdo), Fludarabine (F-araA), Nelerabine (MAY), Zidovudine, Floxuridine (FUDR), β-Thymidine, idoxuridine (IdU), trifluridine (TFT), acedurid (EdU), ribavirin, didanosine (ddl) and Pentostatin.

More preferably, the APIs or intermediates thereof produced using the host cells of present invention, transformed with the recombinant expression vectors, previously described, are selected from: Clofarabine, Cytarabine, Vidarabine, Brivudine, Enocitabine, Zalcitabine, Cladribine, Fludarabine, Nelerabine, Zidovudine, Floxuridine and Pentostatin; yet more preferably the APIs or intermediates thereof produced are selected from Clofarabine, Cytarabine and Zidovudine; and still more preferably the host transformed cells described herein are particularly suitable for industrial production of Clofarabine, Cytarabine and an intermediate of Zidovudine; furthermore preferably Clofarabine or intermediates thereof, yet more preferably Clofarabine.

More preferably, the previously mentioned use is achieved by the production process and variants thereof, also previously detailed, of NAs as APIs or intermediates thereof.

EXAMPLE 1

Cloning and Expression NDTs from *Lactobacillus delbrueckii* Subsp. *lactis* DSM 20072

Cloning.
The gene encoding N-deoxyribosyltransferase from *Lactobacillus delbrueckii* subsp. *lactis* (in GenBank accession number EGD27012.1) was amplified by polymer chain reaction (PCR) from *Lactobacillus delbrueckii* subsp. *lactis* DSM 20072 genomic DNA. The gene was cloned into the polylinker region of the expression vectors: pET22 b(+), using the restriction sites NdeI and SalI The primers used were designed with proper modifications at 5'-ends (see sequences):

```
                                    (SEQ. ID No. 19)
Ldndt2 fw:    5'-CATATGCCAAAAAAGACGATCTACTTC-3'

(SEQ. ID No. 20)
Ldndt2 rv:    5'-GTCGACTTAGTATACGGCACC-3'
```

The corresponding gene for nucleoside 2-deoxyribosyltransferase sequence was amplified by PCR, using the Platinum Taq enzyme (Invitrogen), with the corresponding forward and reverse oligonucleotides (SEQ. ID. From No.19 and No. 20). The amplified 0.-kb product was inserted into a pGEM-T vector. The cloned region was completely sequenced and it was found to be the same to the data bank sequence. The insert DNA was digested with NdeI and SalI and then ligated into an expression vector of pET-22b(+) digested with the same restriction enzymes.

The ligation product was transformed into chemically competent *E. coli* DH5α cells. Positive plasmids were selected and subsequently transformed into BL21(DE3) chemically competent cells.

Expression and Purification of NDT from *Lactobacillus delbrueckii* Subsp. *lactis*

*E. coli* strain bearing the recombinant plasmid were grown aerobically in LB medium supplemented with ampicillin (100 μg ml$^{-1}$) until OD$_{600\ nm}$ of 0.5 was reached.

Overexpression of the protein was achieved by inducing the *E. coli* culture with 0.5 mM isopropyl-1-thio-β-D-galactopyranoside (IPTG) at 37° C. for 4 h. The bacterial cells were harvested by centrifugation at 4° C. at 4,000×g for 20 minutes. Harvested cells were resuspended in 20 ml of Phosphate Buffered Saline (PBS Buffer) for cells collected from one liter cell culture. The cell suspensions were lysed using sonication (Branson Sonifier 450). Cell lysate (supernatant) was obtained by centrifugation at 13000×g for 45 min to obtain an enzyme corresponding to the amino acid sequence SEQ. ID. NO. 2 encoded by nucleotide sequence SEQ. ID. NO. 1 and having NDT activity.

EXAMPLE 2

Cloning and Expression of NDTs from *L. lactis*

Cloning.

The gene encoding N-deoxyribosyltransferase from *Lactococcus lactis* subsp. *lactis* (in GenBank accession number AE006284) was amplified by polymer chain reaction (PCR) from *Lactococcus lactis* subsp. *lactis* genomic DNA. The gene was cloned into the polylinker region of the expression vectors: pET22 b(+), using the restriction sites NdeI and EcoRI The primers used were designed with proper modifications at 5'-ends (see sequences):

```
Llac fw:
                             (SEQ. ID No. 17)
5'-GCCATATGAACAAGTTGTTTAATCAAG-3'

Llac rv:
                             (SEQ. ID No. 18)
5'-GCGAATTCTACTGGTATTTTCCACTATA-3'
```

The corresponding gene for nucleoside 2-deoxyribosyltransferase (NDT) sequence was amplified by PCR, using the Platinum Taq enzyme (Invitrogen), with the corresponding forward and reverse oligonucleotides (SEQ. ID. No.17 and No. 18). The amplified 0.5-kb product was inserted into a pGEM-T vector. The cloned region was completely sequenced and it was found to be the same as the data bank sequence. The insert DNA was digested with NdeI and EcoRI and then ligated into an expression vector of pET-22b(+) digested with the same restriction enzyme.

The ligation product was transformed into chemically competent *E. coli* DH5α cells. Positive plasmids were selected and subsequently transformed into BL21(DE3) chemically competent cells.

Expression and Purification of NDT from *Lactococcus lactis* Subsp. *lactis*

*E. coli* strain bearing the recombinant plasmid were grown aerobically in LB medium supplemented with ampicillin (100 μg ml$^{-1}$) until OD$_{600\ nm}$ of 0.5 was reached. Overexpression of the protein was achieved by inducing the *E. coli* culture with 0.5 mM isopropyl-1-thio-β-D-galactopyranoside (IPTG) at 30° C. for 4 h. The bacterial cells were harvested by centrifugation at 4° C. at 4,000×g for 20 minutes. Harvested cells were resuspended in 20 ml of Phosphate Buffered Saline (PBS Buffer) for cells collected from one liter cell culture. The cell suspensions were lysed using sonication (Branson Sonifier 450). Cell lysate (supernatant) was obtained by centrifugation at 13000×g for 45 min.

EXAMPLE 3

Cloning and Expression of a Nucleoside 2-deoxyribosyltransferase Homologue Enzyme from *T. pendens*

Construction and Transformation of the *Escherichia coli* NDT

Cloning

The sequence (SEQ ID No.5) was retrieved from GenBank (complement strain) and it comes from *Thermofilum pendens* Hrk 5 chromosome. The Tpen_0017 gene locus (NC_008698, Version: NC_008698.1, Region: 14900 . . . 15331) was amplified by polymer chain reaction (PCR) from *Thermofilum pendens* Hrk 5 (DSM 2475) genomic DNA. Full-length 0017 gene was cloned without tags and optionally was cloned as either a C-His6-tagged and N-terminal His6-tagged fusion protein.

The gene was cloned into the polylinker region of the expression vectors: pET102/D-TOPO or pET22 b(+), using the restriction sites NdeI and EcoRI or NdeI and XhoI.

The primers used were designed with properly modifications at 5'-ends (see sequences):

```
Tpen_0017_For:
                             (SEQ. ID No. 7)
5'-catatgaaggtctacctggcg-3'

Tpen_0017_4Rev:
                             (SEQ. ID No. 8)
5'-gaattatgcatgtcaacgctacc-3'

Tpen_0017_For:
                             (SEQ. ID No. 9)
5'-caccatgaaggtctacctggcgg-3'

Tpen_0017_RevI:
                             (SEQ. ID No. 10)
5'-tcattgcatgtcaacgctacc-3'

Tpen_0017_RevII:
                             (SEQ. ID No. 11)
5'-ttgcatgtcaacgctacctg-3'

Tpen_0017_Rev:
                             (SEQ. ID No. 12)
5'-ctcgagtcattgcatgtcaacg-3'

Tpen_0017_2Rev:
                             (SEQ. ID No. 13)
5'-ctcgagttgcatgtcaacgtca-3'

Tpen_0017_3Rev:
                             (SEQ. ID No. 14)
5'-gaattctcattgcatgtcaacgtc-3'

Tpen_0017_4Rev:
                             (SEQ. ID No. 15)
5'-gaattatgcatgtcaacgtcacc-3'

Tpen_0017_5Rev:
                             (SEQ. ID No. 16)
5'-ggaattccgcttgcatgtcaacgctacc-3'
```

The forward primer was designed in order to adapt the start signal to the *E. coli* usage (GTG to ATG). The corresponding gene for Tpen_0017 sequence was amplified by PCR, using the Platinum Taq enzyme (Invitrogen), with the corresponding forward and reverse oligonucleotides (SEQ. ID. From No.7 to No. 16). The amplified fragment was subcloned in pGEM-T Easy and then digested and cloned into the polylinker region of the pET22 b(+) vector which carries the ampicillin resistance gene. The cloned region was completely sequenced and it was found to be the same to the data bank sequence. The ligation product was transformed into chemically competent cells E. coli TOP 10 cells (Invitrogen). Positive plasmids were selected and subsequently transformed into BL21(DE3) chemically competent cells.
Expression and Purification of NDT from T. pendens E. coli strain bearing the recombinant plasmid was grown in LB medium supplemented with ampicillin (100 µg ml$^{-1}$) until OD$_{600}$ nm of 0.5-0.8 was reached. Overexpression of the protein was achieved by inducing the E. coli culture with 1 mM isopropyl-1-thio-β-D-galactopyranoside (IPTG) at 37° C. for 4 h. The bacterial cells were harvested by centrifugation at 4 OC at 4,000×g for 20 minutes. Harvested cells were resuspended in 20 mL of Phosphate Buffered Saline (PBS Buffer) for cells collected from one liter cell culture. The cell suspension was lysed using sonication (Branson Sonifier 450). Cell lysate (supernatant) was obtained by centrifugation at 13000×g for 20 min. Extracts (supernatants) were stored at −80° C.

EXAMPLE 4

N-Deoxyribosyltransferase Assays

The activity assay was performed at 40° C., in 50 mM MES (morpholineethanesulfonic acid) buffer (pH 6.5). Under these conditions, a solution of 10 mM adenine and 10 mM 2'-deoxyuridine was incubated during 10 min. Then, the enzyme was added (2.04 µg of purified enzyme or 30 µl of cell extract) up to a final volume of 240 µl, and the reaction was left to proceed during 5 min. The reaction was quenched through the addition of 240 µL of cold MeOH in an ice bath, and further heated at 95° C. for 5 min. Sample was centrifuged at 9700 rpm for 2 min, and the supernatant was diluted ½ with water. The diluted aliquot was filtered through 0.45 µm hydrophilic filter and then through a 10 KDa Ultrafiltration membrane. The sample was analyzed using a high performance liquid chromatograph (HPLC) with Tracer Excel C18 (Teknokroma, 5 µm, 25×0.46 cm) at 40° C., under MeOH/H$_2$O gradient elution conditions, 1 ml/min flow. Detection was performed at least at 254 nm.

The quantification was performed through calculations on the released base, according to a standard solution of 2'-deoxyadenosine eluted in the same conditions. The enzymatic activity is expressed as, either:

(1) Specific activity (Sp act) as units-mg protein$^{-1}$ (µmoles of 2'-deoxyadenosine·min$^{-1}$·mg$^{-1}$)
(2) Enzymatic activity as units·ml$^{-1}$ (µmoles of 2'-deoxyadenosine·min$^{-1}$·ml$^{-1}$)

wherein one unit of enzyme activity was defined as the amount of enzyme required to produce 1 µmol of product per min under standard conditions described herein.

EXAMPLE 5

Clofarabine Production in Aqueous Media Using NDT Enzyme at 4.5 U/µmol$_{araF}$

A suspension of 20 mM 2-chloroadenine (0.142 g, 0.84 mmol) and 20 mM 2'-fluoro-arabinofuranosyl-2'-deoxyuridine (araF) (0.206 g, 0.84 mmol) in aqueous buffer at pH 6.5 (42 ml) was thermostated at 50° C. during 30 min. Then, NDT enzyme (SEQ ID NO: 2) was added (4.5 U/µmol$_{araF}$, 0.422 mg/ml) dropwise and the reaction was stirred at 50° C. during at least 10 days at the same conditions. Then, the suspension was hot filtered, and the solid was washed and dried. The aqueous filtrate was partially concentrated, cooled down and filtered. The recovered solid was allowed to partially precipitate under basic pH conditions and concentration. Once filtered and washed, the solid may be optionally crystallized or recrystallized using a suitable solvent, such as a polar protic or polar aprotic solvent, in combination with water or a suitable apolar solvent.

EXAMPLE 6

Clofarabine Production in Aqueous Media Using NDT Enzyme at 1.78 U/µmol$_{araF}$ A suspension of 50 mM 2-chloroadenine (0.356 g, 2.1 mmol) and 50 mM 2'-fluoro-arabinofuranosyl-2'-deoxyuridine (araF) (0.517 g, 2.1 mmol) in aqueous buffer at pH 6.5 (42 ml) was thermostated at 50° C. during 30 min. Then, NDT enzyme (SEQ ID NO: 2) was added (1.78 U/µmol$_{araF}$, 0.422 mg/ml) dropwise and the reaction was stirred at 50° C. during at least 10 days at the same conditions. Then, the suspension was hot filtered, and the solid was washed and dried. The aqueous filtrate was partially concentrated, cooled down and filtered. The recovered solid was allowed to partially precipitate under basic pH conditions and concentration. Once filtered and washed, the solid may be optionally crystallized or recrystallized using a suitable solvent, such as a polar protic or polar aprotic solvent, in combination with water or a suitable apolar solvent.

EXAMPLE 8

Clofarabine Production in Aqueous Buffer Containing Organic Solvent Using NDT enzyme at 0.9 U/µmol$_{araF}$ A suspension of 20 mM 2-chloroadenine (10.3 mg, 0.06 mmol) and 20 mM 2'-fluoro-arabinofuranosyl-2'-deoxyuridine (araF) (14.8 mg, 0.06 mmol) in a mixture of aqueous buffer at pH 6.5 and 5% THF (reaction volume 3 ml) was thermostated at 50° C. during 30 min. Then, NDT enzyme (SEQ ID NO: 2) was added (0.9 U/µmol$_{araF}$, 0.088 mg/ml) dropwise and the reaction was stirred at 50° C. during at least 5 days at the same conditions. Then, the suspension was hot filtered, and the solid was washed and dried. The aqueous filtrate was partially concentrated, cooled down and filtered. The recovered solid was allowed to partially precipitate under basic pH conditions and concentration. Once filtered and washed, the solid may be optionally crystallized or recrystallized using a suitable solvent, such as a polar protic or polar aprotic solvent, in combination with water or a suitable apolar solvent.

EXAMPLE 9

Clofarabine Production in Aqueous Media Using NDT Enzyme at 0.9 U/µmol$_{araF}$

A suspension of 100 mM 2-chloroadenine (0.712 g, 4.2 mmol) and 100 mM 2'-fluoro-arabinofuranosyl-2'-deoxyuridine (araF) (1.034 g, 4.2 mmol) in aqueous buffer at pH 6.5 (42 ml) was thermostated at 50° C. during 30 min. Then, NDT enzyme (SEQ ID NO: 2) was added (0.9 U/µmol$_{araF}$, 0.422 mg/ml) dropwise and the reaction was stirred at 50° C. during at least 10 days at the same conditions. Then, the suspension was hot filtered, and the solid was washed and dried. The aqueous filtrate was partially concentrated, cooled down and filtered. The recovered solid was allowed to partially precipitate under basic pH conditions and concentration. Once filtered and washed, the solid may be

EXAMPLE 10

Clofarabine Production Using NDT Enzyme at 12.8 U/μmol$_{araF}$

A suspension of 10 mM 2-chloroadenine (3.47 g, 20.1 mmol) and 10 mM 2'-fluoro-arabinofuranosyl-2'-deoxyuridine (araF) (5.0 g, 20.1 mmol) in aqueous buffer at pH 6.5 (2 L) was thermostated at 50° C. during 30 min. Then, NDT enzyme (SEQ ID NO: 2) was added (12.8 U/μmol$_{araF}$, 0.642 mg/ml) dropwise and the reaction was stirred at 50° C. during at least 3 days at the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

EXAMPLE 11

Clofarabine Production Using NDT Enzyme at 1.2 U/μmol$_{araF}$

A suspension of 50 mM 2-chloroadenine (3.03 g, 17.9 mmol) and 50 mM 2'-fluoro-arabinofuranosyl-2'-deoxyuridine (araF) (4.4 g, 17.9 mmol) in aqueous buffer at pH 6.5 (0.35 L) was thermostated at 50° C. during 30 min. Then, NDT enzyme (SEQ ID NO: 2) was added (1.2 U/μmol$_{araF}$, 0.37 mg/ml) dropwise and the reaction was stirred at 50° C. during at least 4 days at the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

EXAMPLE 12

Clofarabine Production Using NDT Enzyme at 9 U/μmol$_{araF}$

A suspension of 10 mM 2-chloroadenine (0.06 g, 0.35 mmol) and 10 mM 2'-fluoro-arabinofuranosyl-2'-deoxyuridine (araF) (0.09 g, 0.35 mmol) in aqueous buffer at pH 6.5 (42 ml) was thermostated at 50° C. during 30 min. Then, NDT enzyme (SEQ ID NO: 2) was added (9 U/μmol$_{araF}$) dropwise and the reaction was stirred at 50° C. during at least 1 days at the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

EXAMPLE 13

Clofarabine Production Using NDT Enzyme at 1.1 U/μmol$_{araF}$

A suspension of 5 mM 2-chloroadenine and 5 mM 2'-fluoro-arabinofuranosyl-2'-deoxyuridine (araF) in ammonium containing aqueous Tris-HCl buffer was thermostated at 25° C. during 25 min. Then, NDT enzyme (SEQ ID NO: 4) was added (1.1 U/μmol$_{araF}$) dropwise and the reaction was stirred at 25° C. during at least 4 days at the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

EXAMPLE 14

Production of Zidovudine Intermediate Using NDT Enzyme at 0.06 U/μmol$_{araF}$

A suspension of 1 mM thymine and 1 mM 3'-amino-2',3'-dideoxyadenosine in aqueous 50 mM MES buffer was thermostated at 50° C. during 20 min. Then, NDT enzyme (SEQ ID NO: 2) was added (0.06 mg/μmol$_{base}$,) dropwise and the reaction was stirred at 50° C. during at least 1 day under the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

EXAMPLE 15

Production of Zidovudine Intermediate Using NDT Enzyme at 0.14 U/μmol$_{araF}$ and 60 mM Thymine A suspension of 60 mM thymine and 60 mM 3'-amino-2',3'-dideoxyadenosine in aqueous 50 mM MES buffer was thermostated at 50° C. during 20 min. Then, NDT enzyme (SEQ ID NO: 2) was added (0.14 mg/μmol$_{base}$,) dropwise and the reaction was stirred at 50° C. during at least 1 day under the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

EXAMPLE 16

Production of Zidovudine Intermediate Using NDT Enzyme at 0.07 U/μmol$_{araF}$

A suspension of 100 mM thymine and 100 mM 3'-amino-2',3'-dideoxyadenosine in aqueous 50 mM MES buffer was thermostated at 50° C. during 20 min. Then, NDT enzyme (SEQ ID NO: 2) was added (0.07 mg/μmol$_{base}$,) dropwise and the reaction was stirred at 50° C. during at least 1 day under the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

EXAMPLE 17

Production of Zidovudine Intermediate Using NDT Enzyme at 0.14 U/$\mu mol_{araF}$ and 80 mM Thymine A suspension of 80 mM thymine and 80 mM 3'-amino-2',3'-dideoxyadenosine in aqueous 50 mM MES buffer was thermostated at 50° C. during 20 min. Then, NDT enzyme (SEQ ID NO: 2) was added (0.14 mg/$\mu mol_{base_s}$) dropwise and the reaction was stirred at 50° C. during at least 1 day under the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

EXAMPLE 18

Cytarabine Production Using NDT Enzyme at 0.085 U/$\mu mol_{araF}$

A suspension of 1 mM cytosine and 1 mM 1-(B-D-arabinofuranosyl)uracil in aqueous 50 mM MES buffer was thermostated at 50° C. during 30 min. Then, NDT enzyme (SEQ ID NO: 2) was added (0.085 mg/ml) dropwise and the reaction was stirred at 50° C. during at least 1 day under the same conditions. Then, the suspension was hot filtered, and the solid was washed and dried. The aqueous filtrate was partially concentrated, cooled down and filtered. The recovered solid was allowed to partially precipitate and concentrate. Once filtered and washed, the solid was crystallized using a suitable solvent, such as a polar protic or polar aprotic solvent, in combination with water or a suitable apolar solvent.

The invention claimed is:

1. A biocatalytic process for producing active pharmaceutical ingredients (APIs) or intermediates thereof, the process being carried out in an one-step/one-pot reaction, wherein said reaction comprises the addition, in a suitable reaction aqueous medium and under suitable reaction conditions, of an enzyme having nucleoside deoxyribosyltransferase (NDT) activity, either native or recombinant, to a mixture of starting materials comprising i) at least a nucleoside, D isomer of 2'-fluoro-arabinofuranosyl-2'-deoxyuridine, 2'-deoxyuridine, or 3'-amino-2',3'-dideoxyadenosine: and ii) at least a free nucleobase, to be transferred by the enzyme having NDT activity, being 2-chloroadenine, 2-chloroadenine or thymine, respectively, wherein the APIs or intermediates thereof produced are selected from Clofarabine, Cladribine and an intermediate of Zidovudine;

wherein the enzyme having NDT activity is a NDT isolated from *Lactobacillus delbrueckii*; and wherein said NDT is obtained from
- a) *Lactobacillus delbrueckii* nucleotide sequence shown in SEQ ID NO. 1; or
- b) a nucleotide sequence encoding for the amino acid sequence shown in SEQ ID. NO:2, and wherein said Zidovudine intermediate is transformed by azidation into Zidovudine.

2. The process according to claim 1 wherein the API, or intermediates thereof, produced is Clofarabine.

3. The process according to claim 1, wherein the enzyme having NDT activity is a NDT isolated from *Lactococcus lactis*.

4. The process according to claim 3 wherein an NDT is obtained from
- a) *Lactococcus lactis* nucleotide sequence shown in SEQ ID NO. 3 or
- b) a nucleotide sequence encoding for the amino acid sequence shown in SEQ ID. NO:4.

5. The process of claim 1, for production of APIs or intermediates thereof, wherein said APIs or their intermediates are nucleoside analogues (NAs) particularly useful as anti-cancer or anti-viral medicaments selected from Clofarabine, Cladribine and Zidovudine, using a recombinant enzyme having nucleoside deoxyribosyltransferase activity, wherein said recombinant enzyme is characterized by being encoded by a nucleic acid sequence comprising a sequence selected from: SEQ ID No. 1 or SEQ ID No. 3; or a nucleotide sequence encoding for an amino acid sequence selected from: SEQ ID NO:2 or SEQ. ID NO:4.

* * * * *